(12) United States Patent
Provencher et al.

(10) Patent No.: US 9,918,769 B2
(45) Date of Patent: Mar. 20, 2018

(54) INSTRUMENTATION AND TECHNIQUE FOR SIZING A BONE RECONSTRUCTION GRAFT

(71) Applicant: ARTHREX, INC., Naples, FL (US)

(72) Inventors: Matthew T. Provencher, Weston, MA (US); Donald K. Shuler, Naples, FL (US); John Sodeika, Naples, FL (US)

(73) Assignee: ARTHREX, INC., Naples, FL (US)

( * ) Notice: Subject to any disclaimer, the term of this patent is extended or adjusted under 35 U.S.C. 154(b) by 160 days.

(21) Appl. No.: 14/839,001

(22) Filed: Aug. 28, 2015

(65) Prior Publication Data

US 2017/0056085 A1    Mar. 2, 2017

(51) Int. Cl.
| | |
|---|---|
| *A61F 5/00* | (2006.01) |
| *A61B 17/88* | (2006.01) |
| *A61B 90/00* | (2016.01) |
| *A61F 2/46* | (2006.01) |
| *A61B 17/90* | (2006.01) |

(52) U.S. Cl.
CPC .......... *A61B 17/8863* (2013.01); *A61B 90/06* (2016.02); *A61F 2/4644* (2013.01); *A61B 2017/90* (2013.01); *A61B 2090/061* (2016.02); *A61F 2002/4649* (2013.01)

(58) Field of Classification Search
None
See application file for complete search history.

(56) References Cited

U.S. PATENT DOCUMENTS

| | | | |
|---|---|---|---|
| 7,124,762 B2 * | 10/2006 | Carter | A61B 17/15 128/898 |
| 8,257,359 B2 | 9/2012 | Burkhart et al. | |
| 8,617,219 B2 | 12/2013 | Oren et al. | |

OTHER PUBLICATIONS

Matthew T. Provencher, et al., "Anatomic Osteochondral Glenoid Reconstruction for Recurrent Glenohumeral Instability With Glenoid Deficiency Using a Distal Tibia Allograft," Arthroscopy: The Journal of Arthroscopic and Related Surgery, vol. 25, No. 4, Apr. 2009; pp. 446-452.

* cited by examiner

*Primary Examiner* — Sameh Boles
(74) *Attorney, Agent, or Firm* — Carlson, Gaskey & Olds

(57) ABSTRACT

This disclosure details surgical instrumentation and related techniques for performing bone reconstruction surgeries. The surgical instrumentation may be used to size and shape a graft, such as an allograft. The appropriately sized and shaped graft is subsequently used to reconstruct damaged bone. A surgical instrumentation set is used to prepare the graft. The surgical instrumentation set includes a graft workstation, a plurality of sizing blocks and a plurality of cutting blocks.

9 Claims, 18 Drawing Sheets

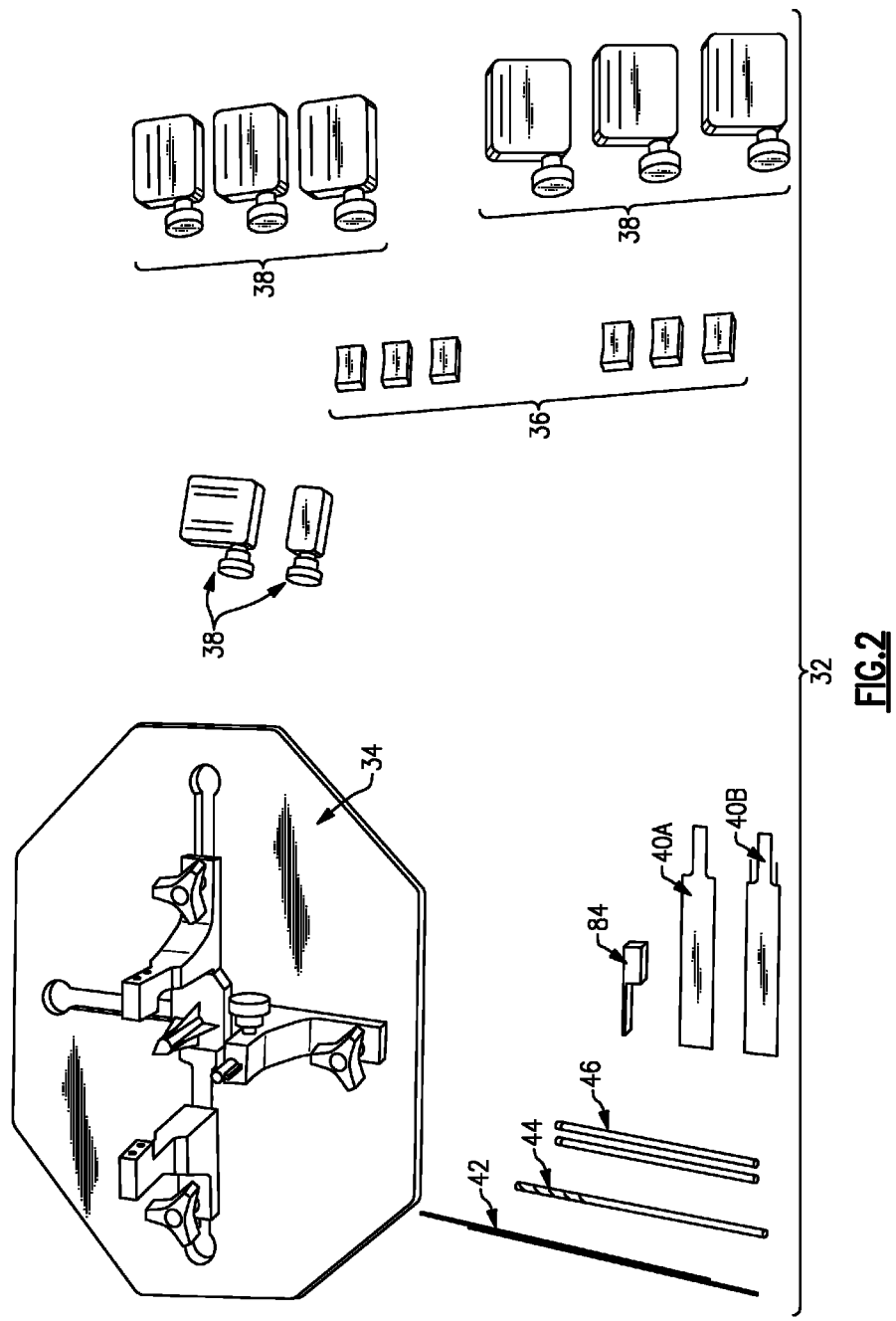

INSTRUMENTATION AND TECHNIQUE FOR SIZING A BONE RECONSTRUCTION GRAFT

BACKGROUND

This disclosure relates to a surgical instrumentation set and associated techniques for performing bone reconstruction surgery.

Repetitive trauma to a joint may cause bone loss. For example, recurrent dislocations of the shoulder joint may result in glenoid bone loss and decreased glenohumeral stability. Current techniques for bony reconstruction of the glenoid include use of a coracoid bone block graft, often referred to as the Latarjet procedure. However, reconstruction of the glenoid to treat glenohumeral instability remains a challenge.

SUMMARY

This disclosure details surgical instrumentation and related techniques for performing bone reconstruction surgeries. The surgical instrumentation may be used to size and shape a graft, such as an allograft. The appropriately sized and shaped graft may subsequently be used to reconstruct damaged bone.

A surgical instrumentation set according to an exemplary aspect of the present disclosure includes, among other things, a graft workstation configured to receive a bone block. The graft workstation includes a cutting jig movable relative to the bone block. A plurality of sizing blocks are configured to estimate a size of a bone graft to be harvested from the bone block. A plurality of cutting blocks are interchangeably connectable to the cutting jig and are each configured to guide at least one cut in the bone block to form the bone graft.

In a further non-limiting embodiment of the foregoing surgical instrumentation set, the bone graft is a distal tibia allograft.

In a further non-limiting embodiment of either of the surgical instrumentation sets, the graft workstation includes a first graft holding post and a second graft holding post.

In a further non-limiting embodiment of any of the surgical instrumentation sets, the first graft holding post and the second graft holding post are slidable within a first slot of a base plate of the graft workstation and the cutting jig is slidable within a second slot of the base plate.

In a further non-limiting embodiment of any of the surgical instrumentation sets, the first graft holding post includes a spiked post configured to receive the bone block.

In a further non-limiting embodiment of any of the surgical instrumentation sets, the plurality of cutting blocks include a first cutting block having a first slot configured to make a vertical cut in the bone graft and a second slot configured to make an angled cut in the bone graft.

In a further non-limiting embodiment of any of the surgical instrumentation sets, the plurality of cutting blocks include a second cutting block configured to make a horizontal cut in the bone graft.

In a further non-limiting embodiment of any of the surgical instrumentation sets, the plurality of cutting blocks include a third cutting block configured to make additional vertical cuts in the bone graft.

In a further non-limiting embodiment of any of the surgical instrumentation sets, a parallel drill guide is configured to retrieve the bone graft from the bone block.

In a further non-limiting embodiment of any of the surgical instrumentation sets, a parallel pin guide, a guide wire, and a drill are configured to aid in preparing the bone graft.

A surgical method according to another exemplary aspect of the present disclosure includes, among other things, securing a bone block to a graft workstation, intraoperatively estimating an amount of bone loss of a bone using a sizing block, and preparing a bone graft to a size and shape that corresponds to the sizing block. The bone block includes a distal tibia allograft.

In a further non-limiting embodiment of the foregoing surgical method, the method includes selecting a first cutting block that corresponds to a size of the sizing block, connecting the first cutting block to a cutting jig of the graft workstation, and making a first cut in the bone block using the first cutting block.

In a further non-limiting embodiment of either of the foregoing surgical methods, the first cut is a vertical cut and the method includes making an angled cut in the bone block using the first cutting block.

In a further non-limiting embodiment of any of the foregoing surgical methods, the method includes removing the first cutting block from a cutting jig of the graft workstation, connecting a second cutting block to the cutting jig and making a horizontal cut in the bone block using the second cutting block.

In a further non-limiting embodiment of any of the foregoing surgical methods, the method includes removing the second cutting block from the cutting jig, connecting a third cutting block to the cutting jig and making additional cuts in the bone block using the third cutting block.

In a further non-limiting embodiment of any of the foregoing surgical methods, securing the bone block to the graft workstation includes driving the bone block onto a spiked post.

In a further non-limiting embodiment of any of the foregoing surgical methods, securing the bone block to the graft workstation includes driving guide pins into the bone block.

In a further non-limiting embodiment of any of the foregoing surgical methods, making the first cut includes guiding a saw through a slot of the first cutting block.

In a further non-limiting embodiment of any of the foregoing surgical methods, the method includes removing a bone graft from the bone block and attaching the bone graft to the bone to reconstruct the bone.

In a further non-limiting embodiment of any of the foregoing surgical methods, the method includes forming holes in a bone graft and fixating the bone graft to the bone by inserting fasteners through the holes and into the bone.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

BRIEF DESCRIPTION OF THE DRAWINGS

FIG. 2 illustrates a surgical instrumentation set for preparing a graft.

DETAILED DESCRIPTION

Figure 1A:
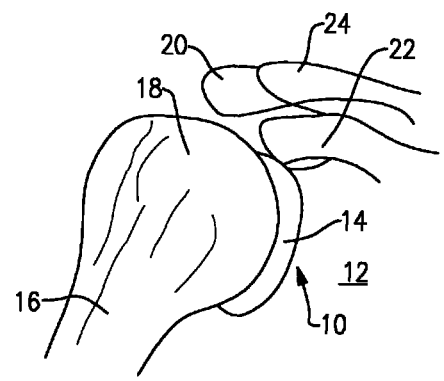
FIGS. 1A and 1B schematically illustrate a glenohumeral joint of a human musculoskeletal system.

This disclosure describes surgical instrumentation and related techniques for reconstructing bone that is afflicted with areas of bone loss. An exemplary technique includes sizing and shaping a bone graft, such as an allograft, which is subsequently used to reconstruct the damaged bone.

In some embodiments, a surgical instrumentation set includes a graft workstation having a cutting jig configured to accept a plurality of interchangeable cutting blocks. The cutting blocks are used to guide a cutting tool for making various cuts into a bone block for sizing and shaping the bone graft. In some embodiments, the bone graft is sized and shaped using the graft workstation to prepare a trapezoidal shaped bone graft. In other embodiments, the bone graft is a distal tibia allograft. These and other features are described in greater detail in the following paragraphs of this detailed description.

FIG. 1 illustrates a joint 10 of the human musculoskeletal system. The joint 10 could be any joint of the musculoskeletal system of the human body; however, in this non-limiting embodiment, the joint 10 is illustrated as the glenohumeral joint of the shoulder. The joint 10 includes multiple bones including a scapula 12 and a humerus 16. Some bones of the joint 10 articulate relative to one another. For example, the joint 10 includes a ball and socket joint formed between a head 18 of the humerus 16 and a glenoid 14, which is a cup-like recession of the scapula 12 configured to receive the head 18. Other bones of the joint 10 include the acromion 20 and the coracoid process 22. A clavicle 24 connects the acromion 20 to the sternum (not shown).

During sporting or other rigorous activities, the humerus 16 may become dislocated or dislodged from the glenoid 14. When dislocation occurs, ligaments and/or other tissues can be torn away from the glenoid 14, resulting in instability of the joint 10. Recurring dislocations may eventually lead to bone loss within the glenoid 14, thereby resulting in further instability.

Figure 1B:
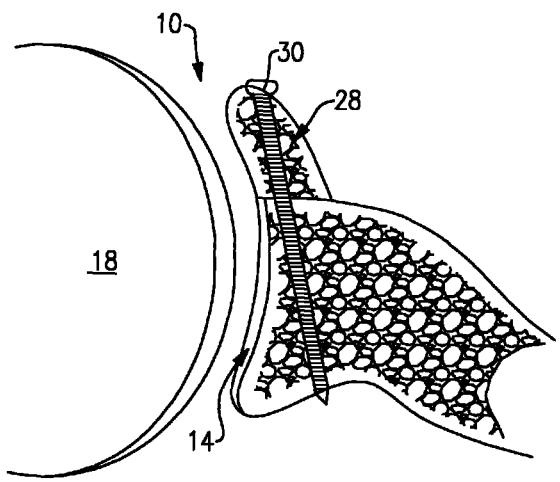

Referring now to FIG. 1B, the glenoid 14 may be reconstructed using a bone graft 28 to stabilize the joint 10. In one non-limiting embodiment, the exemplary bone reconstruction surgeries described throughout this disclosure are performed as open procedures. The bone graft 28 may be attached to the glenoid 14 using one or more fasteners 30 (e.g., screws). This disclosure describes a surgical instrumentation set and technique for preparing the bone graft 28 as part of a bone reconstruction procedure. Although bone reconstruction procedures of the shoulder joint are described throughout this disclosure, this disclosure is not intended to be limited to shoulder reconstructions. In other words, the surgical instrumentation set and techniques described herein could be used to reconstruct any bone of any unstable joint.

FIG. 2 illustrates a surgical instrumentation set 32 for preparing the bone graft 28 (shown in FIG. 1B). For example, the surgical instrumentation set 32 can be employed to size, shape, cut and otherwise prepare the bone graft 28 for subsequent attachment to the damaged portion of the glenoid 14. The exemplary surgical instrumentation set 32 may include a graft workstation 34, a plurality of sizing blocks 36, a plurality of cutting blocks 38, a pair of parallel drill guides 40A (without prongs), 40B (with prongs), guide wires 42, a drill 44, guide pins 46, and a cutter guide 84. In one non-limiting embodiment, the surgical instrumentation set 32 is provided as part of a kit for performing bone reconstruction surgeries. Such a kit could include a greater or fewer number of surgical instruments than is shown in FIG. 2.

The graft workstation 34 provides a work space for safely and accurately preparing the bone graft 28 from a bone block. The sizing blocks 36 may be used to size the bone graft 28 based on an estimated amount of bone loss. In one non-limiting embodiment, six sizing blocks 36 are provided. The sizing blocks 36 may be either 7 mm or 10 mm wide at the articular surface with an opposing surface angle of either 5°, 10° or 15°. Other sizes may also be provided as part of the surgical instrumentation set 32. The cutting blocks 38 may be used to make various cuts in the bone block for sizing and shaping the bone graft 28. The parallel drill guides 40A, 40B, guide wires 42, drill 44, guide pins 46 and the cutter guide 84 may also be utilized as discussed below to help prepare the bone graft 28.

Figure 3A:
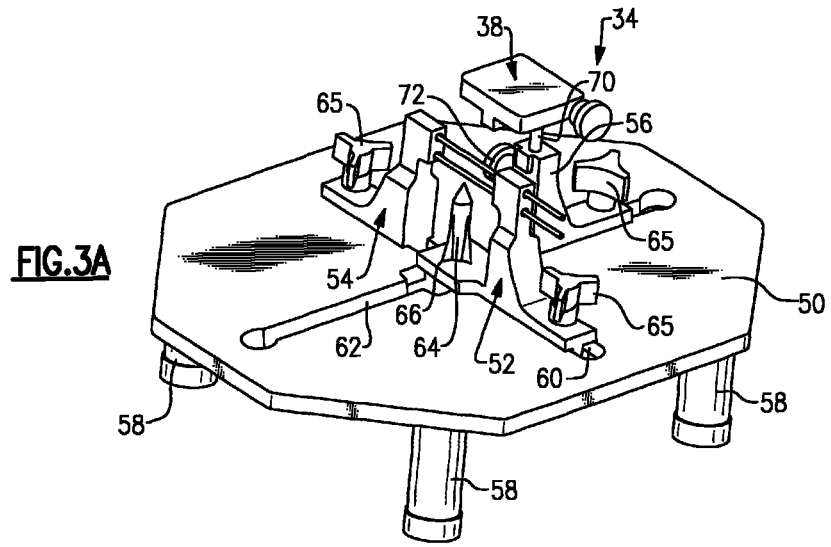
FIGS. 3A and 3B illustrate a graft workstation of the surgical instrumentation set of FIG. 2.
Figure 3B:
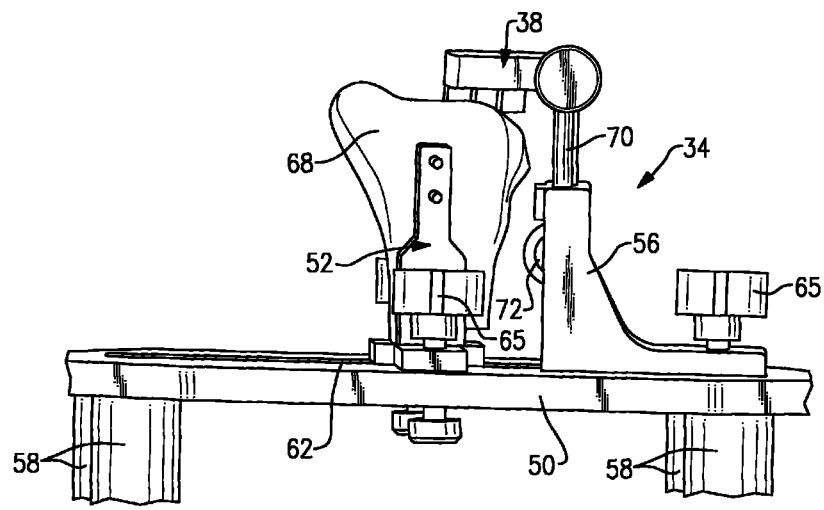

FIGS. 3A and 3B, with continued reference to FIGS. 1A, 1B and 2, illustrate various features of the graft workstation 34 of the surgical instrumentation set 32. The graft workstation 34 may include a base plate 50, a first graft holding post 52, a second graft holding post 54 and a cutting jig 56. The base plate 50 may be elevated above a tabletop or other surface by a plurality of legs 58. A first slot 60 and a second slot 62 are formed in the base plate 50. In one non-limiting embodiment, the first slot 60 and the second slot 62 intersect one another and extend at transverse angles relative to one another.

The first graft holding post 52 and the second graft holding post 54 may be slideably received within the first slot 60 and may each be moved to a desired position relative to the base plate 50. Locking nut assemblies 65 may be used to lock the positioning of each of the first graft holding post 52 and the second graft holding post 54. A spiked post 64 may protrude upwardly from a surface 66 of the first graft holding post 52 and is configured to receive and hold a bone block 68 (see, for example, FIG. 3B).

The cutting jig 56 may be slideably received within the second slot 62 and can be moved to a desired position relative to both the base plate 50 and the bone block 68. In one non-limiting embodiment, the cutting jig 56 is configured to interchangeably receive one of the cutting blocks 38 for harvesting the bone graft 28 from the bone block 68. In another non-limiting embodiment, the cutting jig 56 includes a telescoping arm 70 that is movable to adjust a vertical positioning of the cutting blocks 38 relative to the bone block 68. The telescoping arm 70 may be released for movement relative to the cutting jig 56 by manipulating a handle 72. Another locking nut assembly 65 may be used to lock the positioning of the cutting jig 56 relative to both the base plate 50 and the bone block 68.

FIGS. 4-16 schematically illustrate an exemplary technique for sizing the bone graft 28. Continued reference is made to FIGS. 1A, 1B, 2, 3A and 3B throughout the following description of FIGS. 4 through 16. FIGS. 4 through 16 illustrate, in sequential order, one non-limiting embodiment for preparing the bone graft 28 using the surgical instrumentation set 32. It should be understood; however, that fewer or additional steps than are recited below could be performed and that the recited order of steps is not intended to limit this disclosure.

Figure 4:
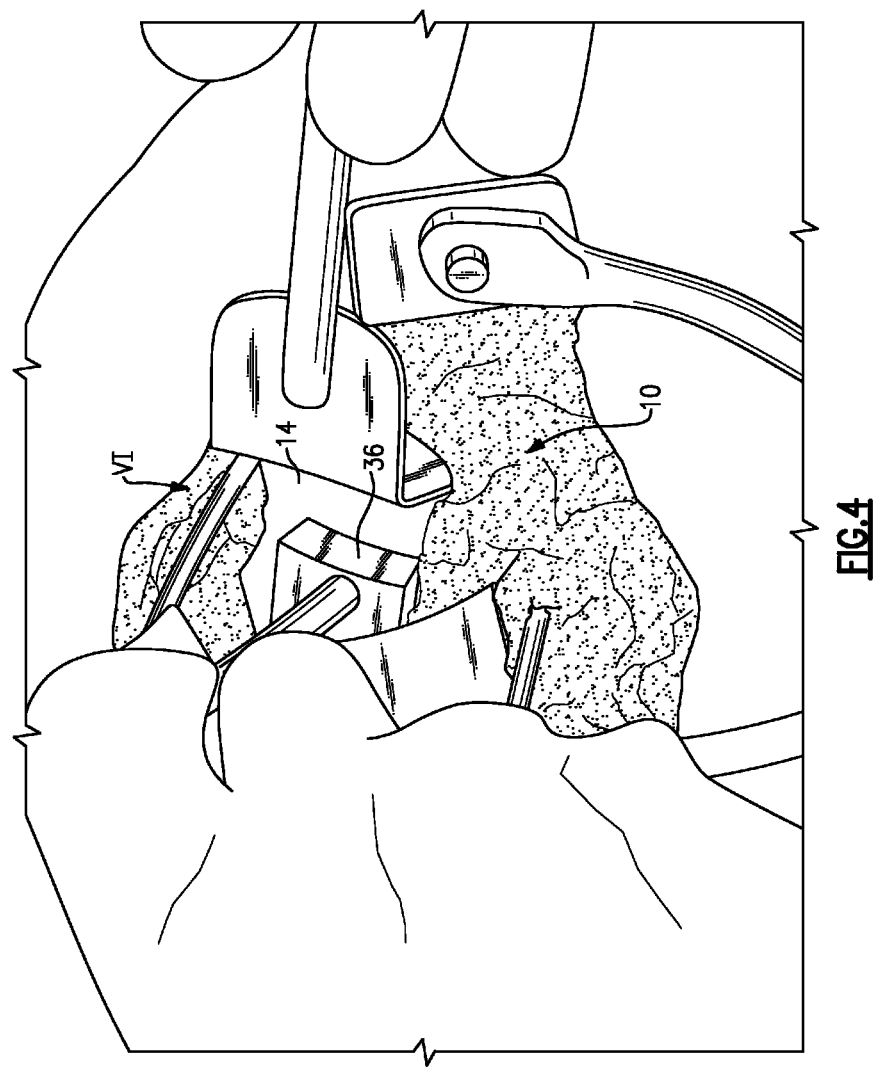
FIG. 4 schematically illustrates the use of a sizing block to identify an amount of bone loss associated with a damaged bone.

Referring first to FIG. 4, a vertical incision VI is made in-line with the face of the glenoid 14 at a location just lateral to the conjoined tendon. The surgeon may inspect the glenoid 14 for bone loss and determine the appropriate size of the bone graft 28 by using the sizing blocks 36. For example, as schematically shown, the sizing blocks 36 may be positioned one at a time within the joint 10 until the sizing block 36 that best approximates the amount of bone loss is chosen. The chosen sizing block 36 indicates to the surgeon the size of the bone graft 28 that is necessary to reconstruct the glenoid 14. The amount of bone loss could alternatively or additionally be confirmed from preoperative CT scans of the joint 10. In one non-limiting embodiment, bone graft reconstruction of the glenoid 14 is performed if bone loss approaches 15% or more at the anterior glenoid surface.

Figure 5:
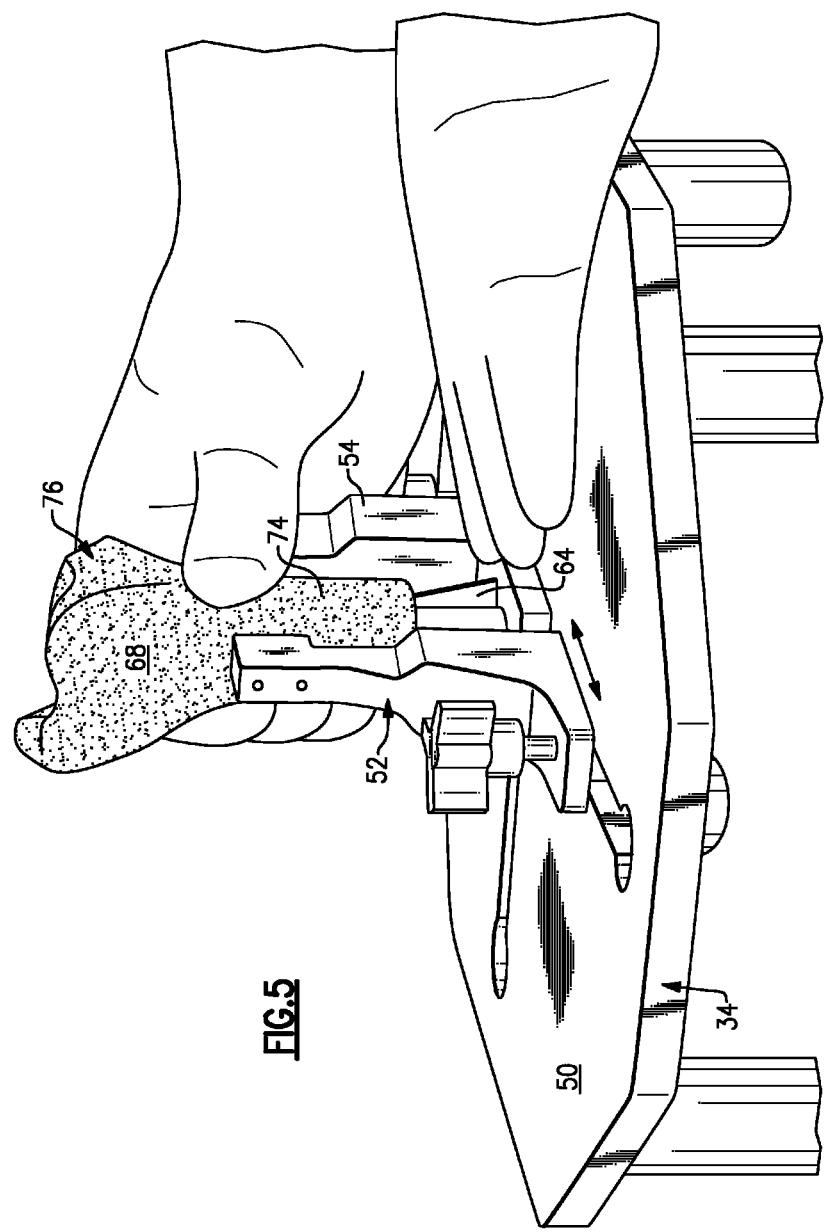
FIG. 5 illustrates positioning of a bone block on a graft workstation.
Figure 6:
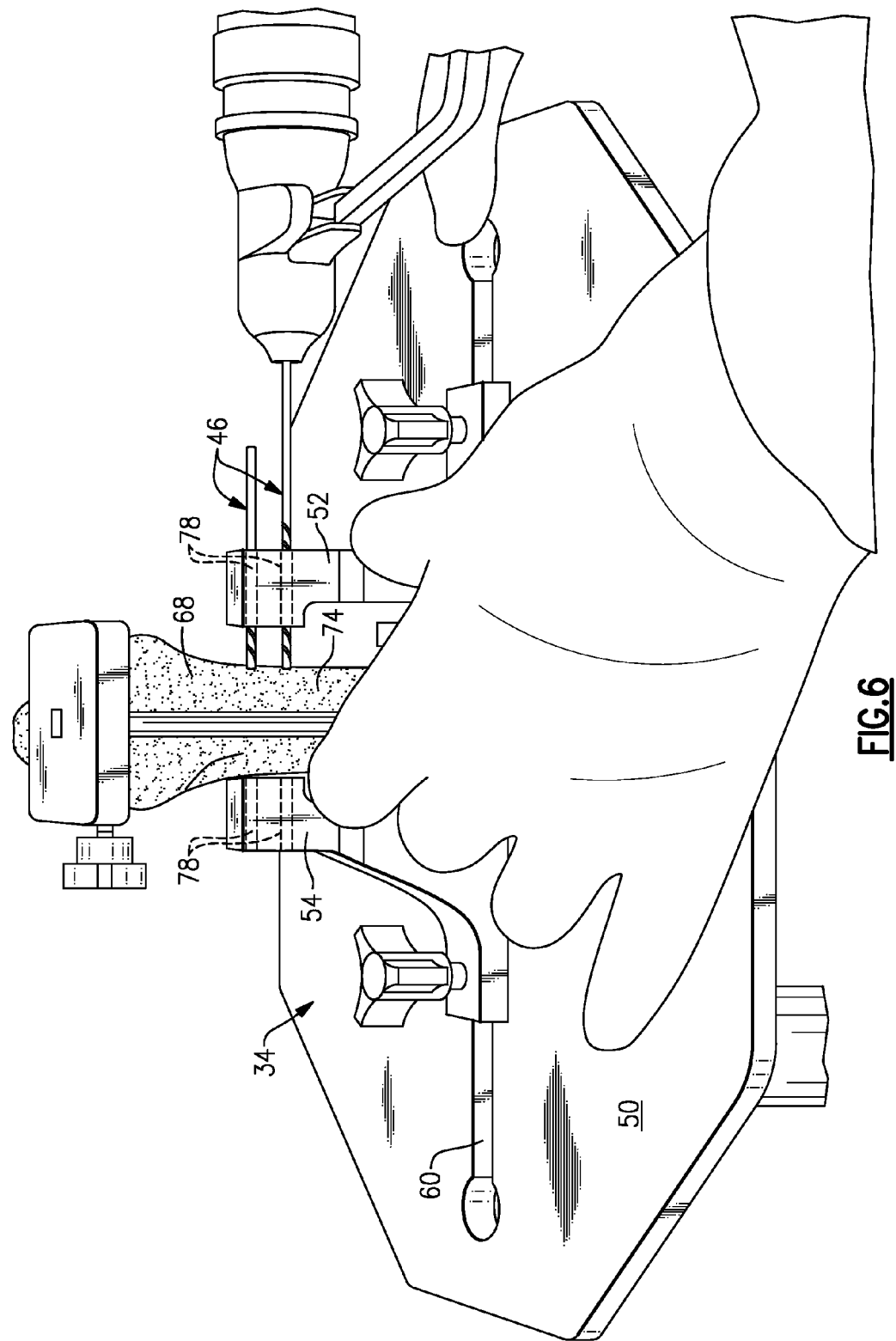
FIG. 6 schematically illustrates securing the bone block to the graft workstation.

Next, as shown in FIGS. 5-6, the bone block 68 is positioned on the graft workstation 34. The bone block 68 may be positioned on the graft workstation 34 by driving a shaft 74 of the bone block 68 onto the spiked post 64 of the first graft holding post 52 and then moving both the first graft holding post 52 and the second graft holding post 54 within the first slot 60 to a desired positioning relative to the bone block 68. The bone block 68 can be adjusted in rotation in multiple planes until its concave surface 76 is positioned about perpendicular to the cutting jig 56 (see FIG. 6). After correct position has been confirmed, guide pins 46 may be passed through the shaft 74 of the bone block 68 via openings 78 formed in the first and second graft holding posts 52, 54 to securely fixate the bone block 68 to the base plate 50 of the graft workstation 34 (see FIG. 6).

In one non-limiting embodiment, the bone block 68 is a distal tibia allograft. Distal tibia allografts are readily available from donor tissue banks and include a radius of curvature that nearly matches the native curvature of the glenoid 14. Therefore, distal tibia allografts are particularly suited for use in reconstructing a damaged glenoid. In one non-limiting embodiment, the bone graft 28 is harvested from the lateral one-third of the distal portion of the bone block 68.

Figure 7:
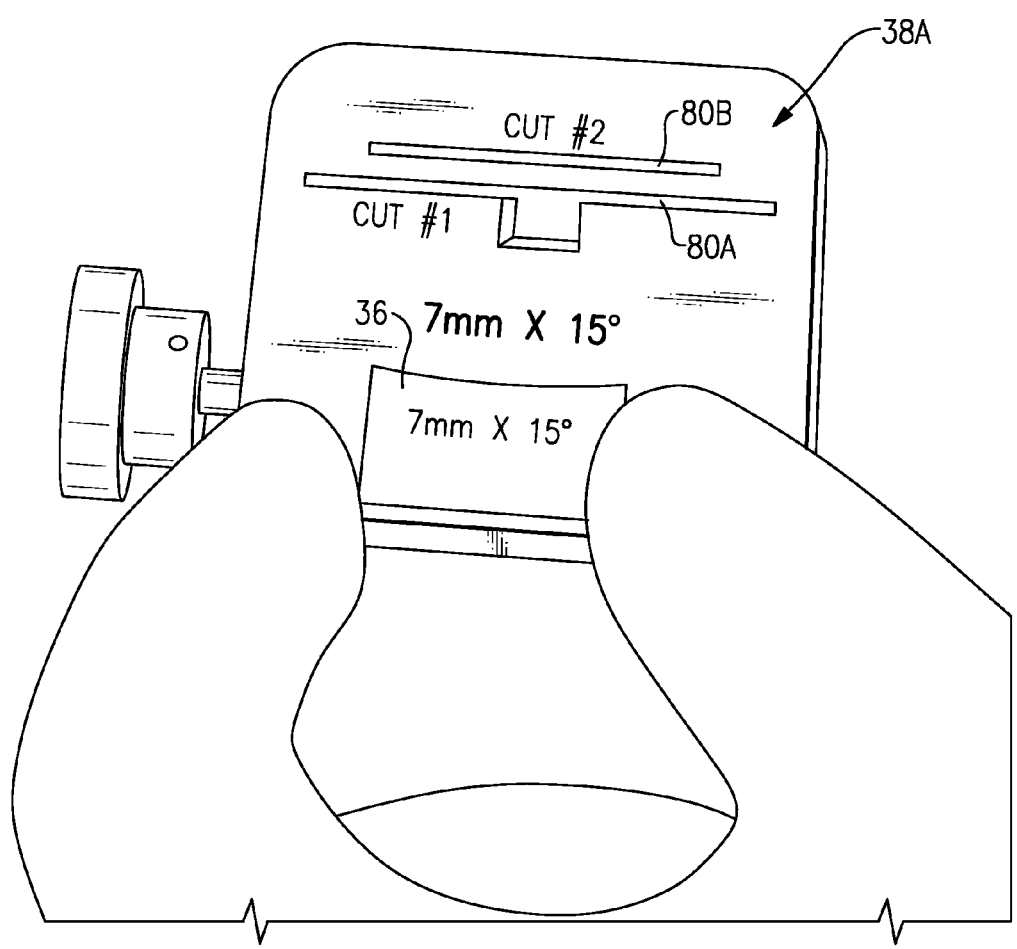
FIG. 7 schematically illustrates the selection of a cutting block.

FIG. 7 schematically illustrates selection of a first cutting block 38A for making multiple cuts in the bone block 68 to size and shape the bone graft 28. The size of the first cutting block 38A corresponds to the size of the sizing block 36 previously used to estimate the amount of bone loss associated with the glenoid 14. For example, if the magnitude of the bone loss is estimated as being approximately 7 mm wide at the articular surface with an opposing surface angle of around 15°, then the cutting block that is marked as 7 mm×15° is selected as the first cutting block 38A.

In one non-limiting embodiment, the first cutting block 38A includes a first slot 80A for making a first cut in the bone block 68 and a second slot 80B for making a second cut in the bone block 68. The first cut may be a vertical cut and the second cut may be an angled cut, as discussed further below.

Figure 8:
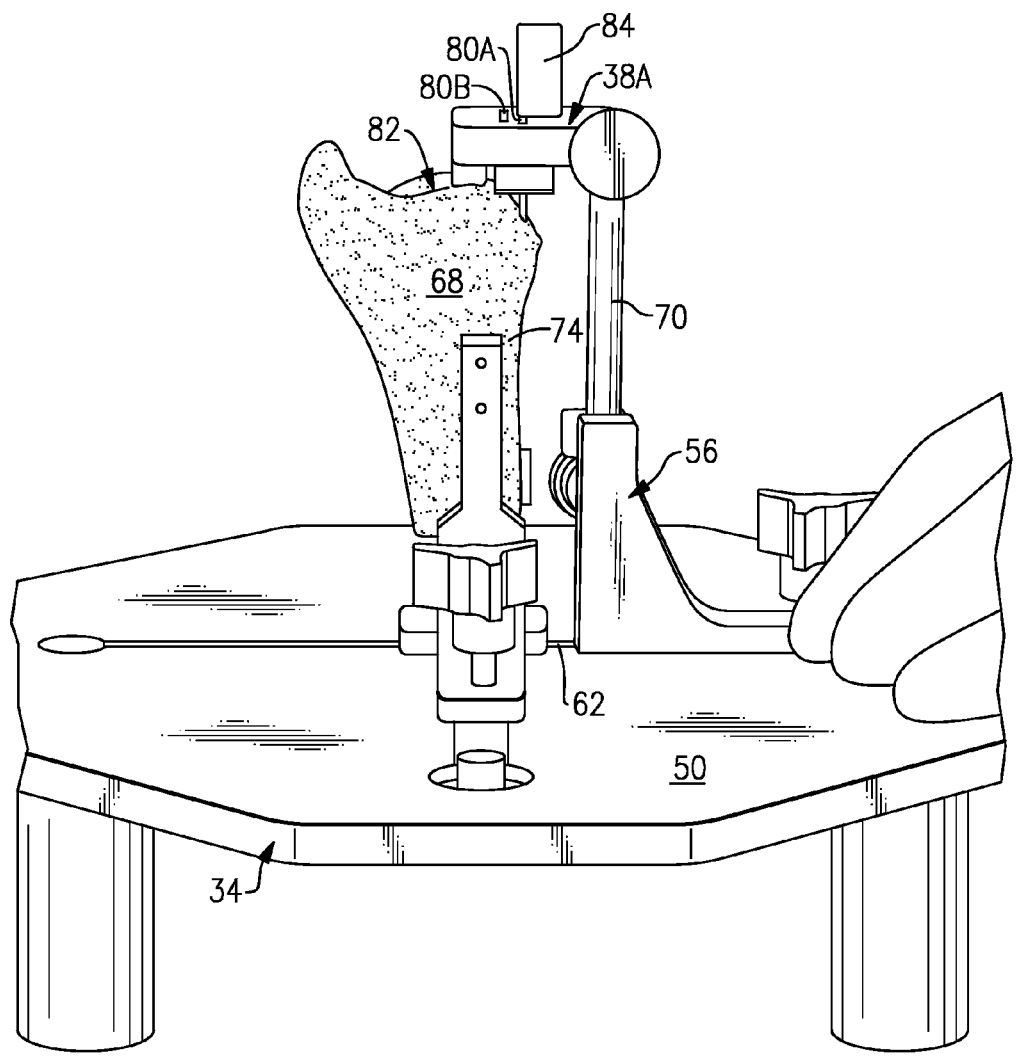
FIG. 8 schematically illustrates positioning of a cutting jig relative to the bone block.
Figure 9:
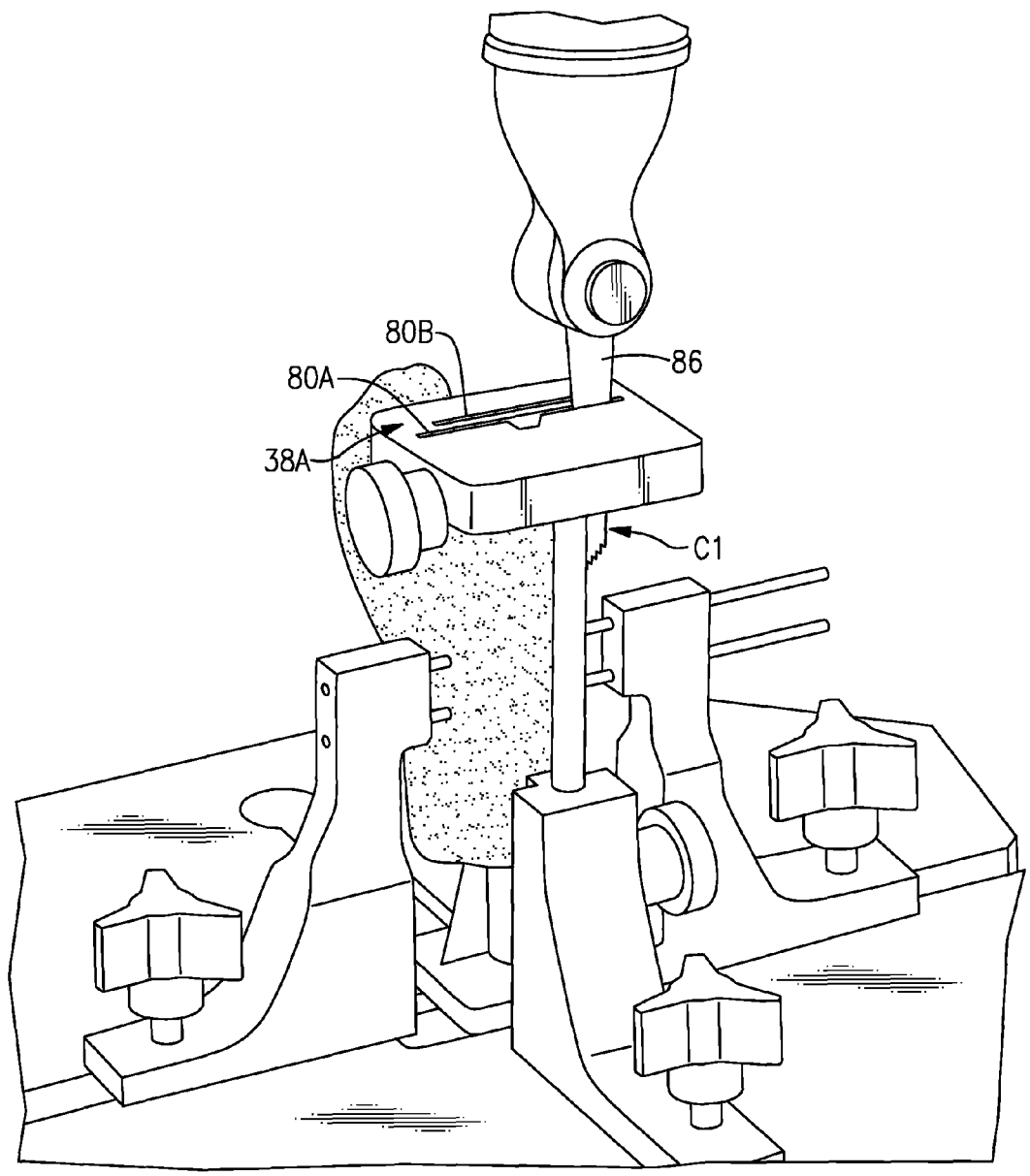
FIG. 9 schematically illustrates creating a first cut in the bone block for forming a bone graft.

Referring to FIG. 8, the first cutting block 38A may be connected to the cutting jig 56 to prepare to make cuts in the bone block 68. The telescoping arm 70 of the cutting jig 56 may then be lowered or raised to move the first cutting block 38A into contact with an articular surface 82 of the bone block 68. The cutting jig 56 may next be moved within the second slot 62 of the base plate 50 of the graft workstation 34 until a cutter guide 84 that is received within the first slot 80A of the first cutting block 38A contacts the shaft 74 of the bone block 68. The cutter guide 84 can then be removed and a saw 86, such as an oscillating saw blade, may be inserted through the first slot 80A to make a vertical cut C1 in the bone block 68 (see FIG. 9). The saw 86 may be moved across an entire width of the first slot 80A to guide the saw 86 as it makes the vertical cut C1. The vertical cut C1 forms a vertical wall of the bone graft 28.

Figure 10:
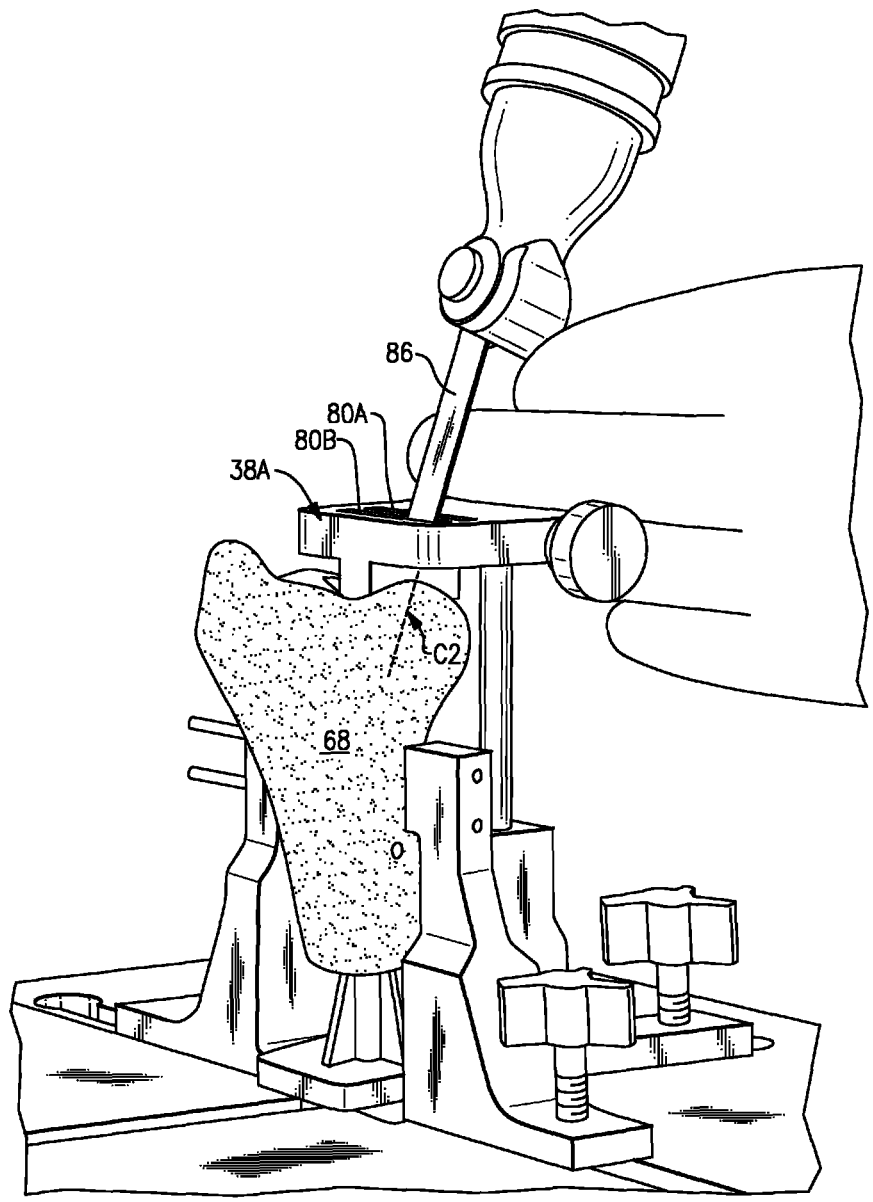
FIG. 10 schematically illustrates creating a second cut in the bone block for forming the bone graft.

Next, as shown in FIG. 10, the saw 86 may be inserted through the second slot 80B to make an angled cut C2 in the bone block 68. The saw 86 may be moved across a width of the second slot 80B to guide the saw 86 as it makes the angled cut C2. The angled cut C2 cuts an angled wall on the bone graft 28 that will eventually mate with the defective portion of the glenoid 14. The first cutting block 38A may be removed from the cutting jig 56 after making the vertical cut C1 and the angled cut C2.

Figure 11:
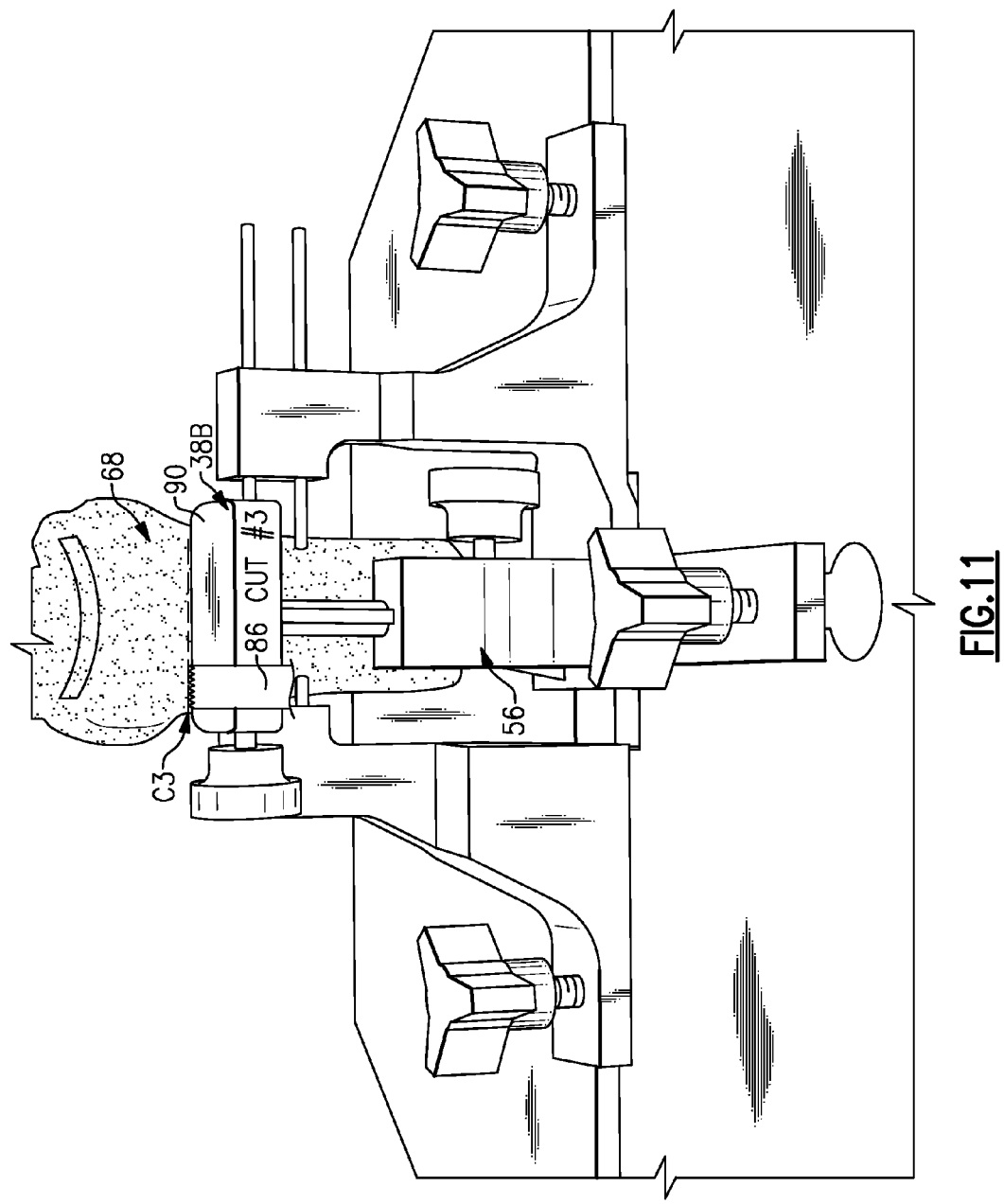
FIG. 11 schematically illustrates creating a third cut in the bone block for forming the bone graft.

A second cutting block 38B may be attached to the cutting jig 56 and subsequently positioned for making a horizontal cut C3 in the bone block 68. This is depicted in FIG. 11. The saw 86 may be guided across a cutting surface 90 of the second cutting block 38B to make the horizontal cut C3. The horizontal cut C3 forms a horizontal wall which establishes the depth of the bone graft 28. In one non-limiting embodiment, the depth of the horizontal cut C3 is approximately 12 mm, although other depths are also contemplated.

Figure 12:
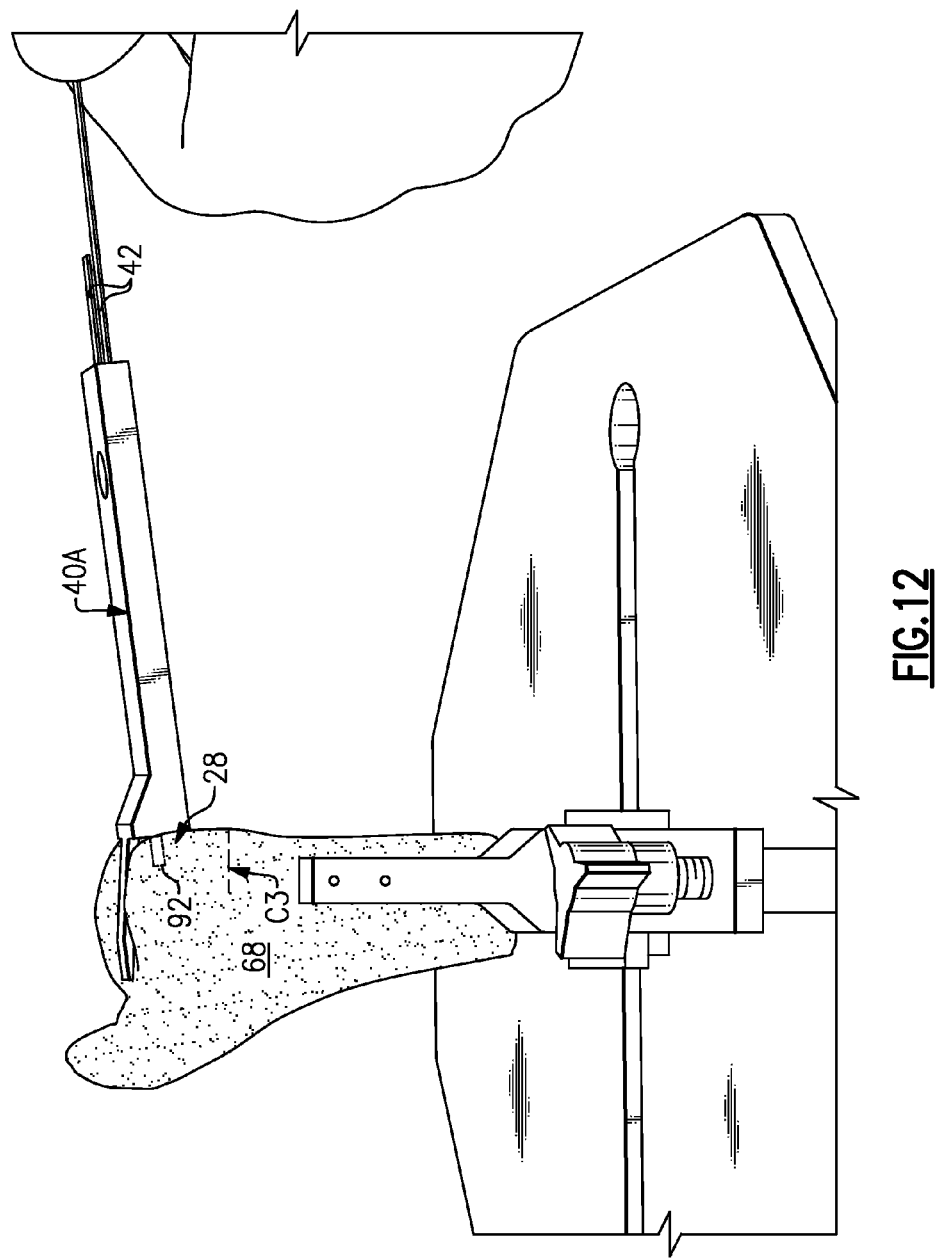
FIG. 12 schematically illustrates the use of a drill guide for forming fastener receiving holes in the bone graft.

The next step of the exemplary technique, shown in FIG. 12, includes drilling holes 92 (best shown in FIG. 16) into the bone graft 28. The holes 92 are subsequently used to aid attachment of the bone graft 28 to the damaged glenoid 14. In one non-limiting embodiment, two holes 92 are formed in the bone graft 28, although any amount of holes may be formed.

The parallel drill guide 40A (without prongs) of the surgical instrumentation set 32 may be used to form the holes 92. In one-non-limiting embodiment, the parallel drill guide 40A is positioned such that guide wires 42 that are passed through the parallel drill guide 40A are positioned just below the articular surface of the bone block 68. The parallel drill guide 40A is removed after insertion of the guide wires 42, and the holes 92 may then be formed by advancing a drill of the surgical instrumentation set 32 over each of the guide wires 42 (not shown).

Figure 13:
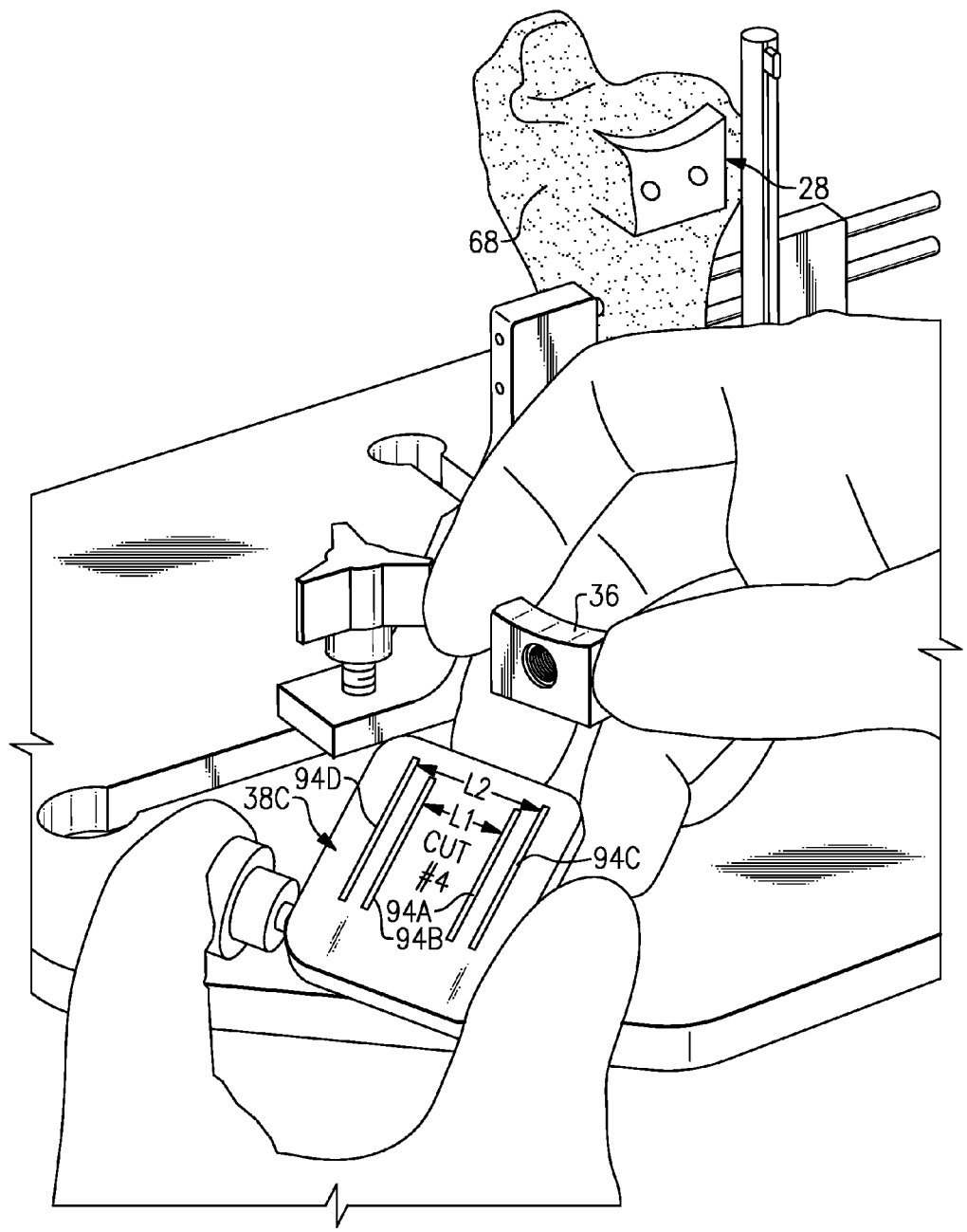
FIG. 13 schematically illustrates the use of a sizing block to determine a length of the bone graft.

FIG. 13 schematically illustrates the selection of a third cutting block 38C for making additional cuts in the bone block 68 to size and shape the bone graft 28. The size of the third cutting block 38C corresponds to the size of the sizing block 36 previously used to estimate the amount of glenoid bone loss. In one non-limiting embodiment, the third cutting block 38C is used to cut the bone graft 28 to the appropriate length.

In one non-limiting embodiment, the third cutting block 38C includes slots 94A, 94B for cutting the bone graft 28 to a length L1 and slots 94C, 94D for cutting the bone graft 28 to a length L2. Additional slots could be provided through the third cutting block 38C for cutting the bone graft 28 to any desired length. In one non-limiting embodiment, length options of 22.5 mm, 14.5 mm or 19.5 mm are provided by the third cutting block 38C. The cuts made through the slots 94A, 94B, 94C, 94D may be vertical cuts, as discussed further below.

Figure 14:
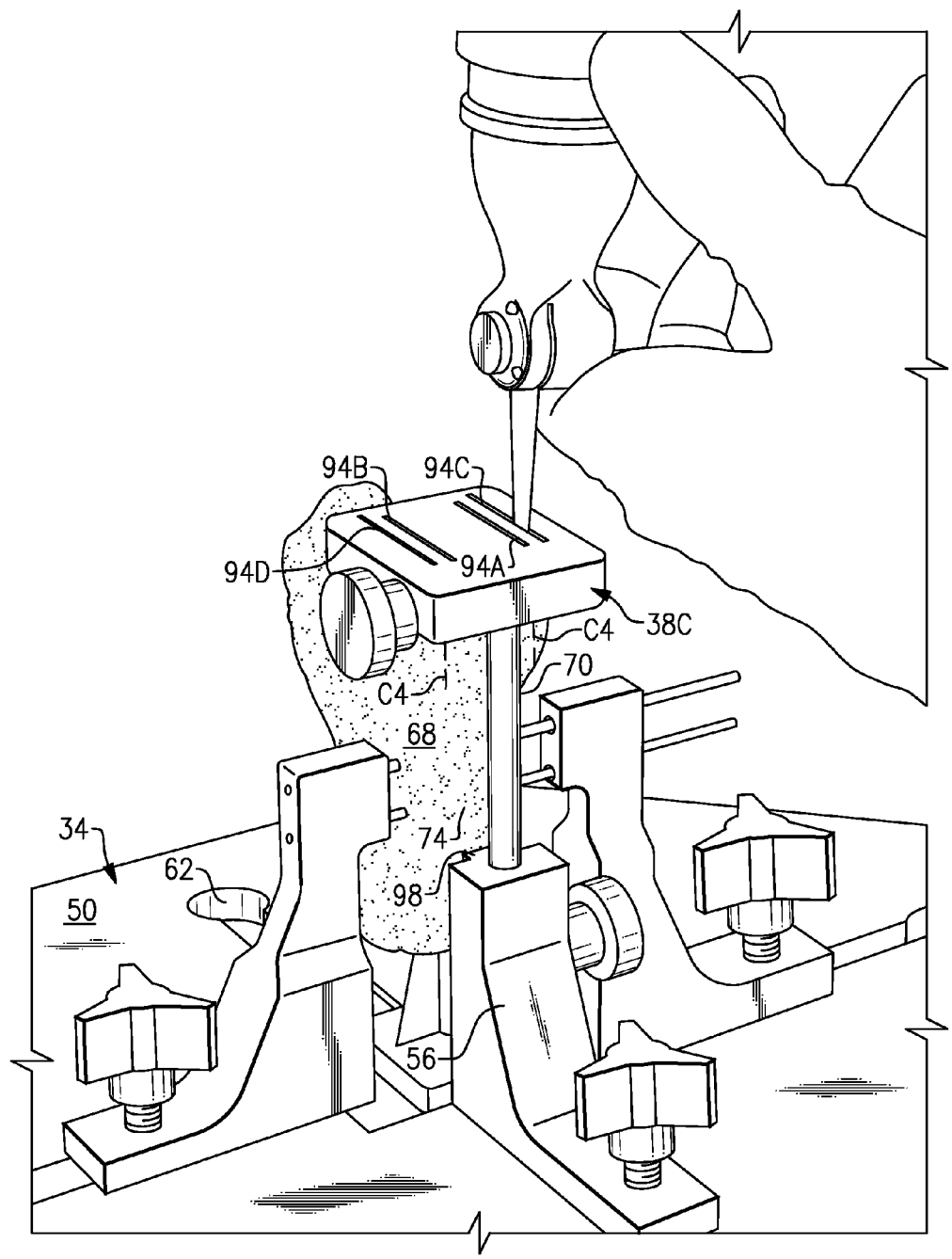
FIG. 14 schematically illustrates creating a fourth cut in the bone block for forming the bone graft.

Referring now to FIG. 14, the third cutting block 38C may be connected to the cutting jig 56. The telescoping arm 70 of the cutting jig 56 may then be lowered or raised to move the third cutting block 38C into a desired position relative to the bone block 68. The cutting jig 56 may also be moved within the second slot 62 of the base plate 50 of the graft workstation 34 until a post 98 of the cutting jig 56 contacts the shaft 74 of the bone block 68. The saw 86 may then be inserted and guided through each of slots 94A, 94B or through each of slots 94C, 94D to make two additional vertical cuts C4 in the bone block 68. The vertical cuts C4 form end walls of the bone graft 28.

Figure 15:
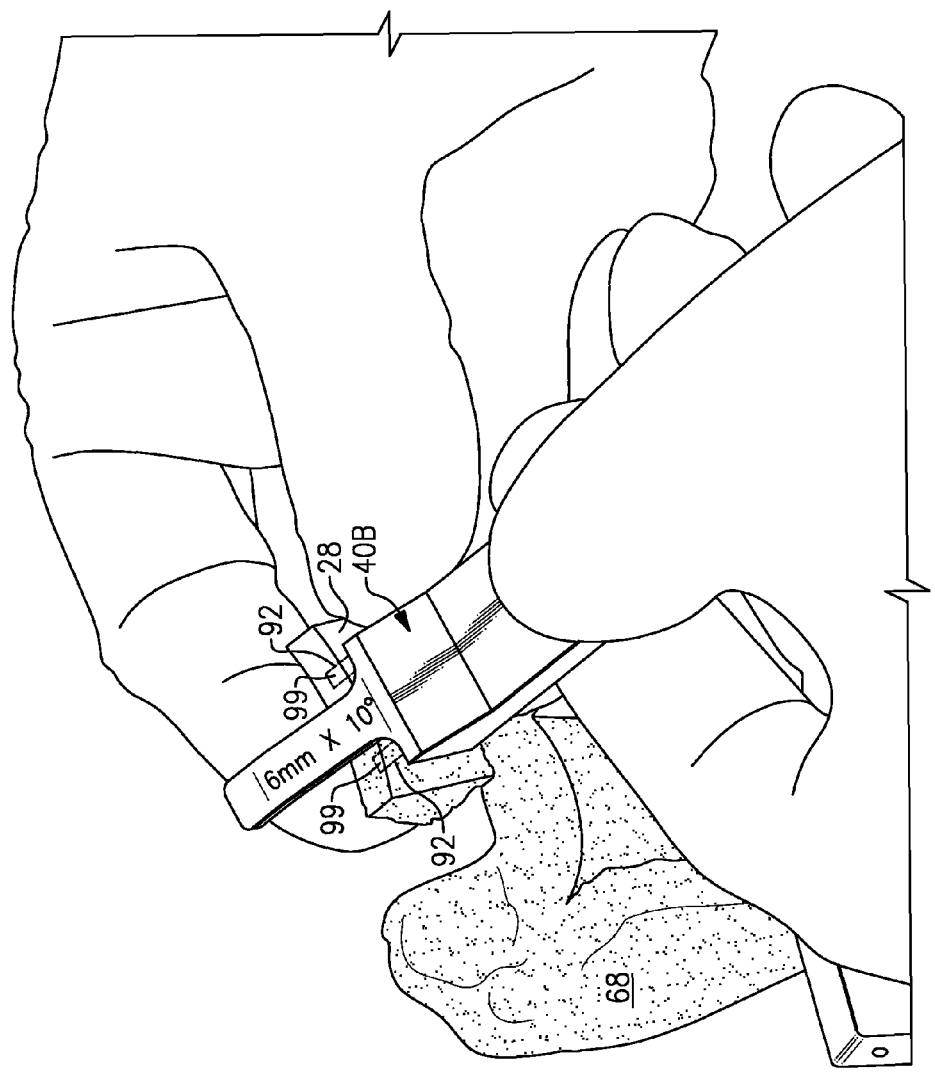
FIG. 15 schematically illustrates removal of the bone graft from the bone block.

Another parallel drill guide 40B (with prongs 99) of the surgical instrumentation set 32 may next be utilized to remove the bone graft 28 from the bone block 68. This is schematically shown in FIG. 15. The prongs 99 of the parallel drill guide 40B are inserted into the previously created holes 92 (best shown in FIG. 16) of the bone graft 28 to extract the bone graft 28 from the bone block 68.

Figure 16:
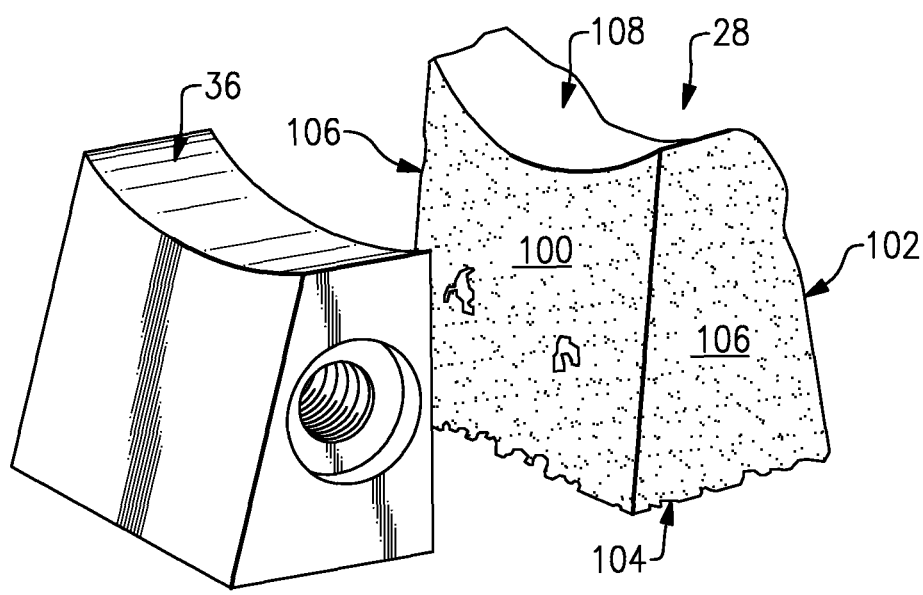
FIG. 16 illustrates a bone graft after removal from a bone block.

FIG. 16 illustrates the bone graft 28 after it has been sized, cut to shape and removed from the bone block 68. In one non-limiting embodiment, the bone graft 28 is generally trapezoidal shaped, although other shapes could alternatively be formed. The bone graft 28 may include a vertical wall 100 (formed by the vertical cut C1), an angled wall 102 (formed by the angled cut C2), a horizontal wall 104 (formed by the horizontal cut C3) and end walls 106 (formed by the additional vertical cuts C4). The bone graft 28 also includes a curved wall 108 that is formed by the native radius of curvature of the articular surface 82 of the bone block 68. As is shown, the size and shape of the bone graft 28 closely matches the size and shape of the sizing block 36 that was previously used to approximate the amount of bone loss (see FIG. 4).

Figure 17:
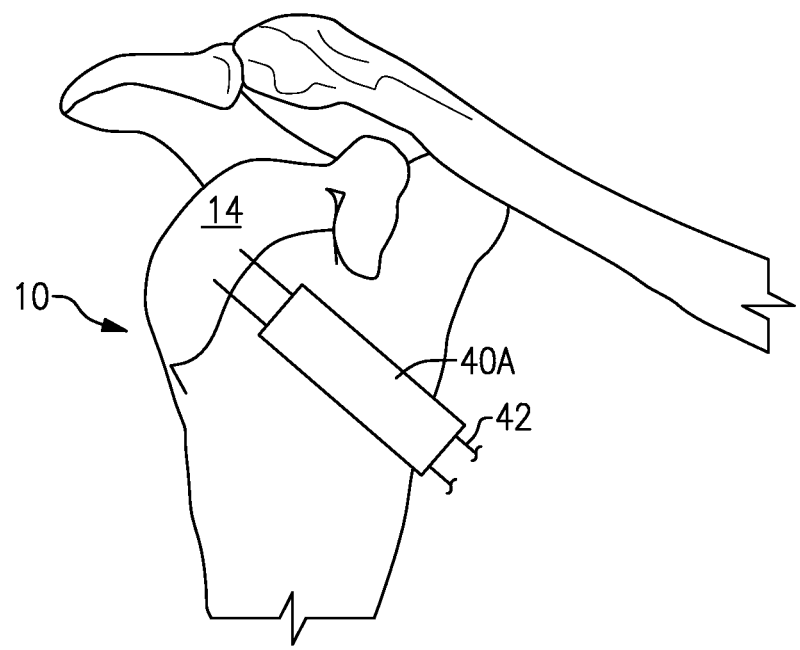
FIG. 17 schematically illustrates placement of guide wires into a joint.
Figure 18:
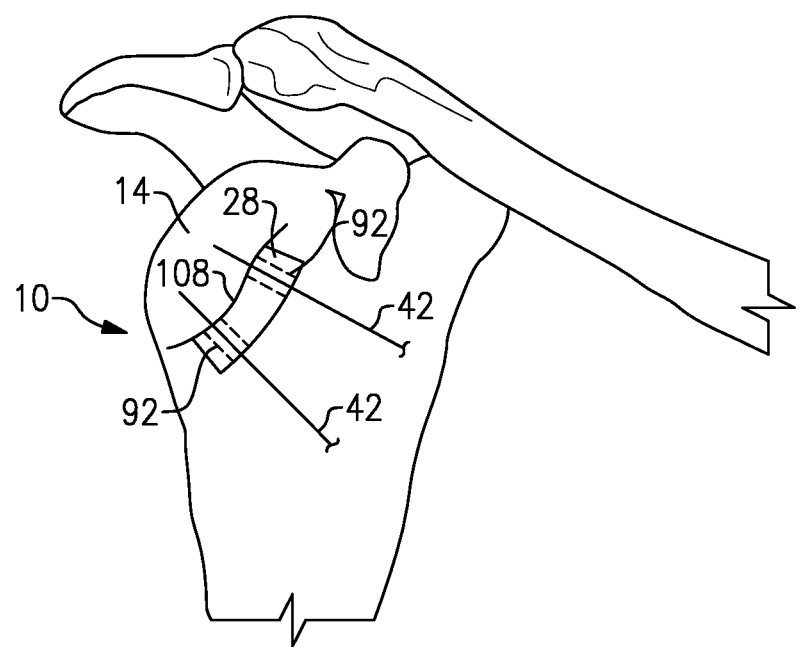
FIG. 18 schematically illustrates placement of the bone graft into the joint.
Figure 19:
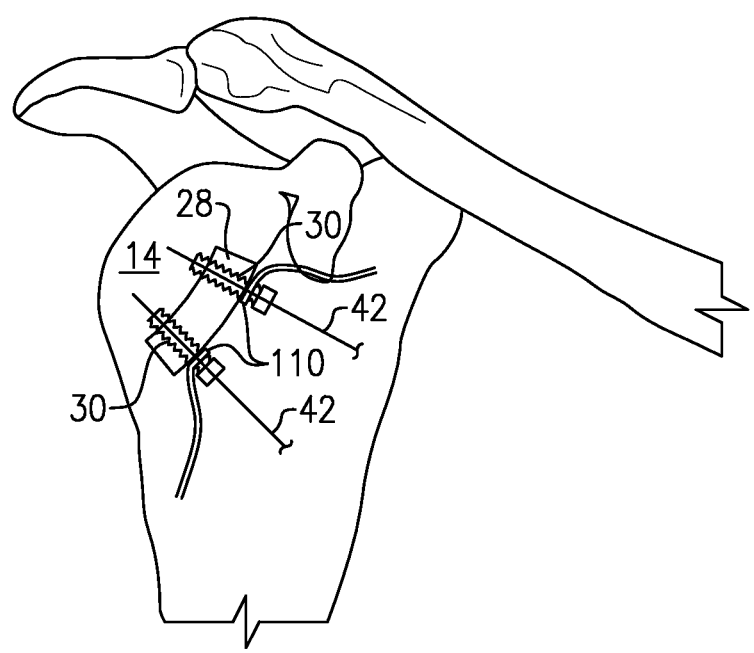
FIG. 19 schematically illustrates attachment of the bone graft to a bone of the joint for reconstructing the bone.

FIGS. 17, 18 and 19 schematically illustrate using the prepared bone graft 28 to reconstruct the glenoid 14 of the joint 10. First, as shown in FIG. 17, the parallel drill guide 40A is used again to place guide wires 42 into the native neck of the glenoid 14 at a location below the articulating surface of the glenoid 14. The parallel drill guide 40A is then removed and the bone graft 28 is introduced over the guide wires 42 by inserting the guide wires 42 through the holes 92 of the bone graft 28 (see FIG. 18). The bone graft 28 is inserted until its curved wall 108 is matched with the articular surface of the glenoid 14.

Finally, as shown in FIG. 19, fasteners 30 may be inserted through the holes 92 of the bone graft 28 to secure the bone graft 28 to the glenoid 14. In one non-limiting embodiment, the fasteners 30 are cannulated screws that may be inserted over the guide wires 42. Suture washers 110 may optionally be used to approximate the joint capsule to the reconstructed glenoid 14. All instruments are then removed and the wound closed to complete the bone reconstruction procedure.

The surgical instrumentation set and techniques of this disclosure enable the safe and precise preparation of a distal tibial allograft for subsequent use to reconstruct damaged bone. Free-handing may therefore be avoided when sizing and shaping the bone graft.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical instrumentation set, comprising:
a graft workstation configured to receive a bone block, said graft workstation including a cutting jig movable relative to said bone block;
a plurality of sizing blocks configured to estimate a size of a bone graft to be harvested from said bone block; and
a plurality of cutting blocks interchangeably connectable to said cutting jig and each configured to guide at least one cut in said bone block to form said bone graft;
wherein said plurality of cutting blocks include a first cutting block having a first slot configured to make a vertical cut in said bone graft and a second slot configured to make an angled cut in said bone graft.

2. The surgical instrumentation set as recited in claim 1, wherein said bone graft is a distal tibia allograft.

3. The surgical instrumentation set as recited in claim 1, wherein said graft workstation includes a first graft holding post and a second graft holding post.

4. The surgical instrumentation set as recited in claim 3, wherein said first graft holding post and said second graft holding post are slidable within a first slot of a base plate of said graft workstation and said cutting jig is slidable within a second slot of said base plate.

5. The surgical instrumentation set as recited in claim 3, wherein said first graft holding post includes a spiked post configured to receive said bone block.

6. The surgical instrumentation set as recited in claim 1, wherein said plurality of cutting blocks include a second cutting block configured to make a horizontal cut in said bone graft.

7. The surgical instrumentation set as recited in claim 6, wherein said plurality of cutting blocks include a third cutting block configured to make additional vertical cuts in said bone graft.

8. A surgical instrumentation set, comprising:
- a graft workstation configured to receive a bone block, said graft workstation including a cutting jig movable relative to said bone block;
- a plurality of sizing blocks configured to estimate a size of a bone graft to be harvested from said bone block;
- a plurality of cutting blocks interchangeably connectable to said cutting jig and each configured to guide at least one cut in said bone block to form said bone graft; and
- a parallel drill guide configured to retrieve said bone graft from said bone block.

9. A surgical instrumentation set, comprising:
- a graft workstation configured to receive a bone block, said graft workstation including a cutting jig movable relative to said bone block;
- a plurality of sizing blocks configured to estimate a size of a bone graft to be harvested from said bone block; and
- a plurality of cutting blocks interchangeably connectable to said cutting jig and each configured to guide at least one cut in said bone block to form said bone graft; and
- a parallel pin guide, a guide wire, and a drill configured to aid in preparing said bone graft.

* * * * *